United States Patent
Marchetti et al.

(10) Patent No.: US 9,603,357 B2
(45) Date of Patent: Mar. 28, 2017

(54) METHOD AND DEVICE TO EVAPORATE ACTIVE INGREDIENTS FROM A LIQUID SOLUTION

(71) Applicant: ZOBELE HOLDING SPA, Trento (IT)

(72) Inventors: Fabio Marchetti, Trento (IT); Cedric Morhain, Barcelona (ES); Franco Zobele, Trento (IT); Stefano Deflorian, Trento (IT)

(73) Assignee: ZOBELE HOLDING SPA, Trento (IT)

( * ) Notice: Subject to any disclaimer, the term of this patent is extended or adjusted under 35 U.S.C. 154(b) by 0 days.

(21) Appl. No.: 14/694,069

(22) Filed: Apr. 23, 2015

(65) Prior Publication Data

US 2015/0230455 A1    Aug. 20, 2015

Related U.S. Application Data

(63) Continuation of application No. 12/526,960, filed on Mar. 2, 2010, now abandoned.

(30) Foreign Application Priority Data

Feb. 13, 2007   (ES) .................................. 200700384

(51) Int. Cl.
```
A61L 9/00      (2006.01)
A62B 7/08      (2006.01)
A01M 19/00     (2006.01)
B67D 3/00      (2006.01)
A01N 25/18     (2006.01)
A01M 1/20      (2006.01)
A61L 9/03      (2006.01)
A61L 9/12      (2006.01)
B05B 12/02     (2006.01)
C11B 9/00      (2006.01)
```

(52) U.S. Cl.
CPC ........... *A01N 25/18* (2013.01); *A01M 1/2033* (2013.01); *A01M 1/2044* (2013.01); *A01M 1/2072* (2013.01); *A01M 1/2077* (2013.01); *A61L 9/03* (2013.01); *A61L 9/037* (2013.01); *A61L 9/12* (2013.01); *A61L 9/122* (2013.01); *A61L 9/127* (2013.01); *B05B 12/02* (2013.01); *C11B 9/00* (2013.01)

(58) Field of Classification Search
CPC ........ A61L 9/122; A61L 2/22; A01M 1/2022; A01M 1/2033; B01D 1/0082
USPC ............ 422/5, 120, 123–125, 298, 305–306; 362/96, 392; 43/132.1, 129, 124; 392/390, 386; 222/187

See application file for complete search history.

(56) References Cited

U.S. PATENT DOCUMENTS 4,642,165 A * 2/1987 Bier ..................... B01D 1/0082
                                                  202/205

* cited by examiner

Primary Examiner — Monzer R Chorbaji
(74) Attorney, Agent, or Firm — Cantor Colburn LLP

(57) ABSTRACT

A method to evaporate active ingredients from a liquid solution, in which said liquid solution includes a solvent and at least one type of active ingredient, the method including dispensing in controlled time periods doses of said liquid solution on a liquid retaining support, where the solvent is evaporated from the support such that only the active ingredient remains on the support, and where the active ingredient is evaporated from the support after most of the solvent has evaporated.

12 Claims, 2 Drawing Sheets

METHOD AND DEVICE TO EVAPORATE ACTIVE INGREDIENTS FROM A LIQUID SOLUTION

CROSS REFERENCE TO RELATED APPLICATIONS

Figure 1:
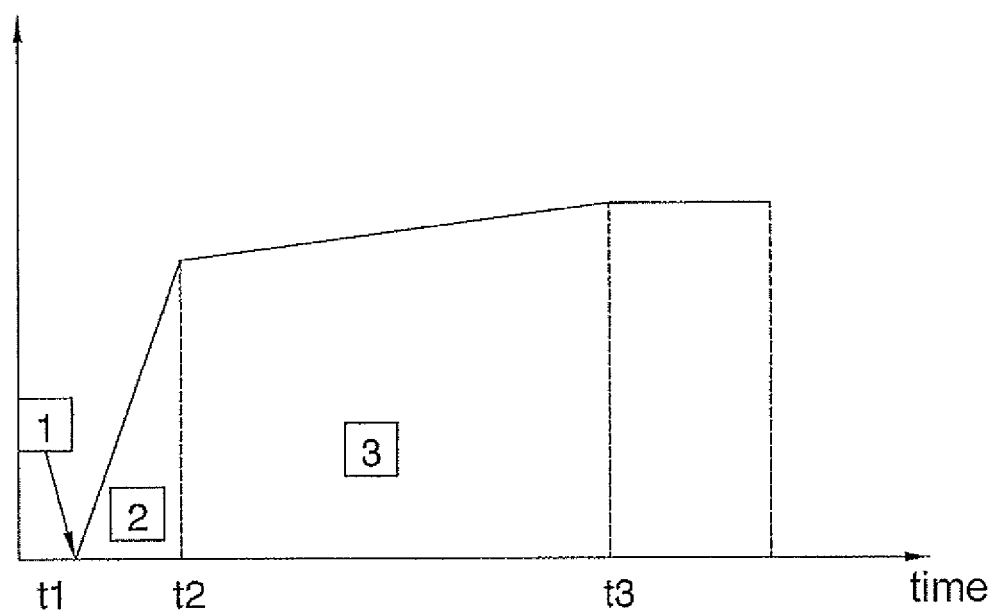

This application is a continuation of U.S. patent application Ser. No. 12/526,960 filed on 13 Aug. 2009, which is the U.S. National Phase of International Patent Application Number PCT/EP2008/051627 filed on 11 Feb. 2008, which claims priority to Spanish Patent Application Number P200700384 filed on 13 Feb. 2007, where the entire contents of all of said applications are herein incorporated by reference.

TECHNICAL FIELD OF THE INVENTION

The present invention relates to a method and a device to evaporate low volatility active substances or ingredients from a liquid solution. The invention is preferably used to evaporate an insecticide substance at low temperature or even at room temperature.

More specifically, the invention includes distributing in the air active ingredients in a controlled manner to control the efficacy of the effect of the active ingredient considering the effective time of evaporation of the liquid, such that the beneficial effects of the active ingredients can be offered to the user as long as possible.

The field of application of the present invention is the industrial sector dedicated to the devices that evaporate volatile products such as perfumes, deodorants, odor and smoke neutralizes, bactericides, insect repellents and air fresheners for interiors in general.

BRIEF DESCRIPTION OF RELATED ART

In dispensing volatile substances to perfume or purify the air of a room, there are many situations in which it is desirable and even necessary to supply one or more doses of product during a more or less long time interval, in order to then stop diffusing the product until another later time. This is the case, for example, of air fresheners for bathrooms, where it is desirable to release a small dose for a few instants and in which no more product is consumed until the user needs it again inside the bathroom. The same happens with insecticides, which are also used during certain times of the day but not continuously, and they are not needed for the rest of the time.

Multiple devices are currently known which manually or automatically allow diffusing the desired active ingredients of a liquid compound by means of a timer, spraying the liquid in an individual dose only at certain instants chosen by the user because the user actuates the spray himself or herself or without any assistance from the user, having previously programmed the timer periodically activating the spraying of the product.

However, these aerosol devices may not be completely effective or inexpensive because the effects of the active ingredients are concentrated in the instant in which the spraying starts and then decrease rapidly. It is therefore convenient for the liquid not to be directly distributed to the air but to a retaining element allowing a gradual evaporation and therefore a more continuous supply of said active ingredients. To date, known evaporators incorporating an absorbent element made of porous material containing the volatile substances are disposable devices having the drawback that said element is impregnated in the factory during the process for manufacturing the product, such that the user receives the element impregnated only with the active ingredients because the solvent spontaneously evaporates beforehand, part of the active ingredient possibly having evaporated during the product storage period. Once most of the active ingredient has evaporated, the device loses its efficiency and must be replaced by a new one.

Several types of diffusers of low volatility active ingredients, such as insecticides, are known, among which electrical devices which can be plugged into a socket can be mentioned; such devices are made up of a bottle with a liquid solution formed by a solvent plus a small percentage of an active ingredient, as well as a wick partly housed inside the bottle allowing said liquid to rise to an upper part of the wick by capillarity means; the wick is subjected to a high temperature to cause the evaporation of the solvent and of the active ingredient. A temperature between 120 and 150° C. is generally required to achieve an unacceptable evaporation rate and suitable biological efficiency for eliminating flies and mosquitoes. This temperature range is much higher than the temperature used in air freshener or perfuming devices using the same evaporation technique (approximately 70° C.) but is a must to evaporate the insecticide active ingredient. In addition, electrical portable devices are also known in which the volatile substance is in solid form, fixed upon a porous support. In the process for manufacturing said support, an amount of a liquid solution is metered on the support such that said support is impregnated with said solution formed by a solvent and the active ingredient. The solvent subsequently evaporates such that when the support is marketed it is impregnated only with the active ingredient. In these devices, once the solvent has evaporated, only the active ingredient in liquid or solid state remains on the support, such that the active ingredient is able to evaporate at low temperature or even at room temperature. Due to low consumption required, these types of device can be manufactured and marketed with a battery supply. The great drawback of these devices is that they by no means show the remaining amount of substance to be evaporated and therefore the remaining duration and the time of protection against mosquitoes for the user, in the case of an insecticide diffuser.

Some devices have attempted to solve this drawback, for example, the device disclosed in U.S. Pat. No. 6,484,438 in which a second reservoir with a volatile product without activity has been added. However, this type of solution is not reliable, because if the physical properties of the two substances have been adjusted so that they evaporate in the same time period, this will happen only in certain environmental temperature and humidity conditions which will have been considered normal while defining the product. In reality, the product can be used in different places and in different seasons of the year, therefore the environmental conditions can be substantially different from those defined as normal, which will involve a lag between the evaporation of the indicator liquid and of the active ingredient.

BRIEF SUMMARY OF THE INVENTION

The present invention solves the technical drawback set forth by means of the inventive subject-matter comprised in the attached independent claims.

One of the aspects of the invention includes of a three step evaporation method during the use of the device by the consumer or user. The method comprises the following phases:

1) metering of a liquid solution upon a liquid retaining support, in which said liquid solution comprises a solvent and at least one type of active ingredient, 2) evaporation of the solvent, 3) evaporation of the active ingredient, The invention takes into account that as long as the solvent has not evaporated, the active ingredient is not able to evaporate without a high temperature input, which is incompatible with the implementation of a portable battery-powered device The present invention thus considers step 2 as especially relevant, therefore a complete evaporation of the solvent from the support is assured before dispensing a new dose of liquid solution.

The method object of the invention is based on the periodic metering of a dose of liquid solution, either by means of impulse activation by the user or by means of an automatic cyclic function in which activation means cause the dispensing of a dose. In any case, means are provided which prevent a new dose from being dispensed until most of the solvent of the previous dose has evaporated.

Therefore, a first aspect of the invention relates to a method to evaporate active ingredients from a liquid solution, which comprises dispensing in controlled time periods doses of said liquid solution upon a liquid retaining support, such that first the solvent evaporates from said support, only the active ingredient remaining on the support. Subsequently, in the absence of the solvent, the active ingredient is able to evaporate by itself, and therefore the active ingredient evaporates from the support after most of the solvent has evaporated.

The evaporation of the solvent and of the active ingredient can occur spontaneously or can be controlled to accelerate the process, for example, by applying an air stream on the support and/or by applying heat, either during the evaporation of the solvent to reduce the duration of phase 2 or also during phase 3. The solvent and/or the active ingredient can be heated at low temperature during their evaporation, for example at a temperature less than 100° C., less than 70° C. or even at room temperature.

The time periods between doses are controlled in the method such that each dose of the liquid solution is dispensed on said support at an instant in time after the evaporation of most of the active ingredient of the previous dose from the support. A dose is thus prevented from being dispensed on the support when the active ingredient retained therein from the previous dose has still not evaporated, The time periods between doses are controlled by means of a timer device, preferably an electronic timer which is associated with electromechanical means to allow dispensing a dose of liquid solution after the established time period between doses. The time necessary to evaporate the solvent and the time of evaporation of the active ingredient are determined by the manufacturer according to the substances used and the evaporation conditions for each practical implementation of the invention, such that the electronic timer is programmed, or designed in the case of a mechanical timer, to be activated in a time period similar to or greater than that necessary to evaporate most of the solvent and active ingredient. After this time, the timer activates electronic and/or mechanical means which enable dispensing a new dose of liquid solution. Therefore, during the time period in which the timer is not activated, the liquid dispensing means are blocked and cannot dispense doses.

After activating the timer and subsequently enabling the dispensing means, a dose of liquid solution can be dispensed by impulse activation by the user at the time when the user considers it necessary to dispense a new dose. Alternatively, a dose of liquid solution can be dispensed automatically, for which purpose there are mechanical means controlled by an electronic circuit which act on the dispensing means after the established time period between doses. In another aspect, the invention consists of a device to evaporate active ingredients from a liquid solution, having a casing with an opening allowing the passage of air, and a reservoir containing said liquid solution. The device comprises at least one liquid retaining support and dispensing means arranged in the casing at a distance and in a suitable position for dispensing doses of said liquid solution on said support. The device further has a timer adapted to allow the operation of said dispensing means in selected time periods, said time periods being greater than the time necessary for evaporating most of the solvent and active ingredient from the support.

The timer device is programmed to a time period corresponding to the time between the metering of two consecutive doses, said time period being similar to the time necessary for evaporating the solvent and then the active ingredient from the support.

The invention mainly improves two critical points in the performance of the volatile product: on one hand, it prevents impregnating the porous material with the liquid in the factory, such that the user can use the effects of the in situ transfer of the liquid to the evaporator support, because all the active ingredient dispensed is used since nothing is lost during the product storage time, or even in the manufacture from when the liquid is dispensed until the product is packaged.

The device of the invention can be manufactured in a simple, inexpensive manner in order to form a portable and easy to handle device, with the possibility of being reused with the incorporation of refills of the reservoir of the liquid solution.

BRIEF DESCRIPTION OF THE DRAWINGS

To complement the description being made and with the aim of aiding to better understand the features of the invention according to a preferred practical embodiment thereof, a set of drawings is attached as an integral part of said description, in which the following is shown with an illustrative and non-limiting character:

FIG. 1 shows a representative graph of the duration times of the three phases of the evaporation method of the invention, corresponding to a dispensed dose of liquid solution. The vertical y-axis indicates the amount of evaporated product and the horizontal x-axis corresponds to time.

FIG. 2 shows in FIG. 2(*a*) a perspective view of a preferred embodiment of the device of the invention without the upper half of the casing in order to show the components housed inside and illustrate the connection between the pushbutton and the spray. FIG. 2(*b*) shows a rear view of the device shown in FIG. 2(*a*).

DETAILED DESCRIPTION OF THE INVENTION

The method of the invention is based on the discontinuity of the metering, for which the metering can occur by a technique known in the state of the art, for example by means of: dripping, by means of a spray or aerosol, or by means of breaking capsules or microcapsules containing the liquid solution. There are optionally evaporation means such as a low consumption heater, i.e. a low temperature heater, a fan or a combination of both elements. These evaporation means can work continuously or discontinuously, for example they can be activated at the same time a dose is dispensed.

The device can be a known device provided with absorption means for absorbing the liquid by capillarity, such as a wick for example, in which the capillary transport is slow enough to allow the interruption of the feed of the liquid in the evaporation area when the evaporation means are activated, If the amount of evaporated solvent is not substituted by more solvent, the active ingredient present alone in the wick will evaporate.

FIG. 1 shows a three step or phase evaporation cycle. Phase 1, consisting of the metering of an amount of solution, occurs almost instantaneously at instant t1. Phase 2 corresponds to a high evaporation rate of the solvent between instants t1 and t2 in a short time period, and finally phase 3 consists of a low evaporation rate of the active ingredient between instants t2 and t3. The next dose of liquid solution can only occur after instant t3.

In practice, evaporation processes logically do not occur uniformly on the entire evaporation surface due to the different evaporation conditions, such that it is possible that while certain areas of the evaporation surface are in phase 2, other areas are in phase 3.

The duration of phase 2 has been especially designed so that it is as fast as possible, as until the solvent has evaporated, the activity caused by the active ingredient is very low or nil and therefore the efficiency of the product is virtually nil. It can be considered that phase 2 ends when most of the solvent has evaporated, i.e., when the amount of solvent present in most of the evaporation area is so small that the active ingredient is able to evaporate in an effective manner. In phase 3, the active ingredient present in the evaporation area without solvent evaporates, and the amount of this active ingredient decreases until the evaporation rate is not enough to ensure the necessary biological efficiency to kill insects, for example. The transition between phases naturally does not occur instantaneously, but rather it is a gradual process depending on the particular evaporation conditions, it can therefore be considered that the duration of phase 3 starts with the beginning of the evaporation of the active ingredient in an effective amount and ends when the amount of this ingredient present in the evaporation area is no longer enough to ensure biological efficiency.

The duration between the metering of two consecutive doses is controlled, such that a dose is not metered as long as phase 3 of the previous dose has not ended. If the next dose is metered before phase 2 of the previous dose ends, the active ingredient will virtually still not have evaporated. On the other hand, if the next dose is metered a long time after phase 3 of the previous dose has ended, i.e. long after the active ingredient has evaporated, the efficiency of the device will be nil for a long time period during which the user will have no protection against mosquitoes, for example.

The invention has means for preventing the premature interruption of phase 2, for example, in the event that the user, with the intention of increasing the efficiency, activates the device for a second time to dispense another dose of the liquid. In such case, the effect would be opposite to that desired, i.e., the efficiency will be nil. Indeed, if the metering is activated again during the duration of phase 2, the active ingredient will never be alone and is therefore not able to evaporate. Furthermore, the new phase 2 will be longer than that determined, because more amount of solvent will have to be evaporated, the amount of solvent already existing from the first metering and the amount of solvent provided with the second metering.

To prevent this situation, the invention incorporates means preventing premature metering. By way of example, these means can be:

electronic means; an electronic timer disconnecting or blocking the metering means for a minimum time period, mechanical means: an activation button with a long period for recovering the initial position once it has been pressed, The present invention provides the shortest possible duration for phase 2 because during phase 2 the efficiency of the device is virtually nil. The duration of phase 2 can be reduced using a high volatility solvent. According to the present invention, a high volatility solvent can consist of a solvent or a mixture of solvents selected to obtain a vapor pressure at room temperature that is equal to or greater than 0.08 mmHg.

In another preferred embodiment, the duration of phase 2 can be reduced by increasing the concentration of active ingredient in the solution, because with less amount of solvent, less time is necessary to evaporate it. It has been found that an optimal composition can be obtained with 5 to 70% w/w of active ingredient and preferably in a range comprised between 20 to 65% w/w.

In another preferred embodiment, the duration of phase 2 is reduced by increasing the evaporation area for the liquid, which can be obtained for example by means of:

metering of small liquid droplets, metering upon a wide area of the liquid retaining support, metering on a high roughness support, —arranging the support in an inclined manner in relation to the metering direction of the liquid, such that the excess liquid will flow down along the surface using a low surface tension solvent, such that the tendency to form droplets decreases, which involves less surface per unit of volume. In the present invention, a low surface tension solvent must be understood as a solvent or a mixture of solvents selected to achieve a surface tension at 25° C. that is equal to or less than 26 mM/m.

in another preferred embodiment, the duration of phase 2 is reduced by reducing the absorption capacity of the support, i.e. preventing the support material from acting as a reservoir of the solvent and the latter being more exposed. For example, in the present invention it has been found that an optimal degree of porosity of the support for obtaining the desired effect is obtained with a material with a liquid absorption capacity of less than 1 $g/cm^3$, preferably less than 0.1 $g/cm^3$.

In another preferred embodiment, the duration of phase 2 is reduced by using a three phase emulsion. For example, said emulsion can be formed by a first solvent A compatible with the active ingredient that is dissolved in it, plus a solvent B in which the active ingredient is not soluble. Both solvents can be mixed together. Some examples of suitable solvents for solvent A are organic solvents such as isoparaffins, propylene glycol ethers, dearomatized hydrocarbons, naphthenic hydrocarbons and acetone. Some examples for solvent B are: water, low molecular weight alcohols such as ethanol and methanol. The amount of solvent A is preferably less than 30% w/w.

In other examples conventional surfactants or surface-active agents can be used, including anionic surfactants, ionic surfactants, amphoteric surfactants and any combination of the above.

In another preferred embodiment, the duration of phase 2 is reduced by using a solvent in which the active ingredient is not soluble, such that when the active ingredient in solid state is arranged in suspension in the solvent, the solvent and active ingredient separation process is faster. Some suitable solvents for this function are water, low molecular weight alcohols such as ethanol and methanol and any mixture thereof. Conventional surfactants, for example, can also be used, including anionic surfactants, ionic surfactants, amphoteric surfactants and any combination of the above.

Nevertheless, despite reducing the duration of phase 2, this phase will continue to exist even though it is for a short time period, during which virtually nil efficiency is obtained. In the case of practical, high-efficiency demanding applications, the existence of phase 2 would not be acceptable, even if it had a very small duration.

For these types of applications, the invention provides a device provided with at least two evaporation areas in which the doses of liquid solution are dispensed in a coordinated manner in the two different liquid retaining supports at different instants in time, such that the active ingredient without solvent is always available in at least one of said supports, i.e. the three phase evaporation occurs in an alternating manner. In this device, the beginning of the cycle will correspond to the metering of the liquid on a first evaporation surface {phase 1} and the active ingredient will evaporate by itself from a second evaporation surface {phase 3). Therefore, when the active ingredient is on the second evaporation surface (end of phase 3), phase 2 on the first surface will have ended and this evaporation surface will be ready for a new phase 3. In the case of an automatic and timed function, a new cycle will start by metering on the second surface and evaporating from the first surface.

Figure 2A:
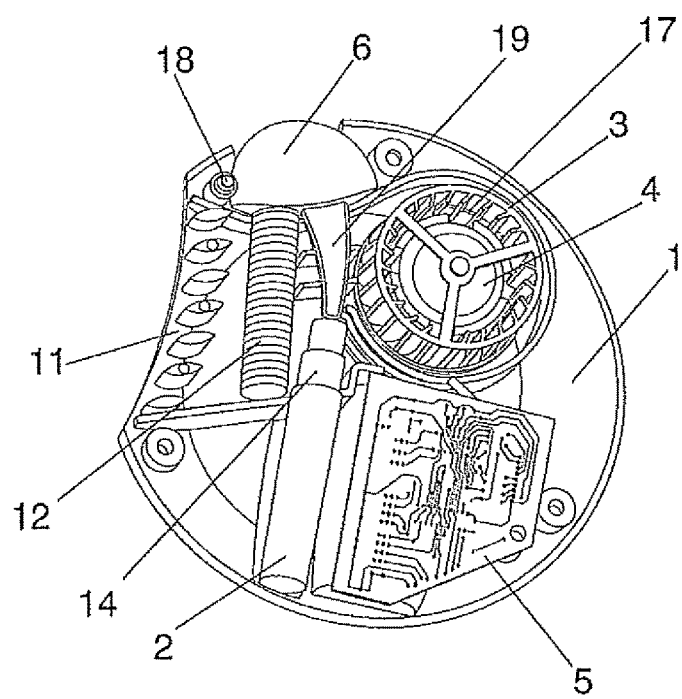
Figure 2B:
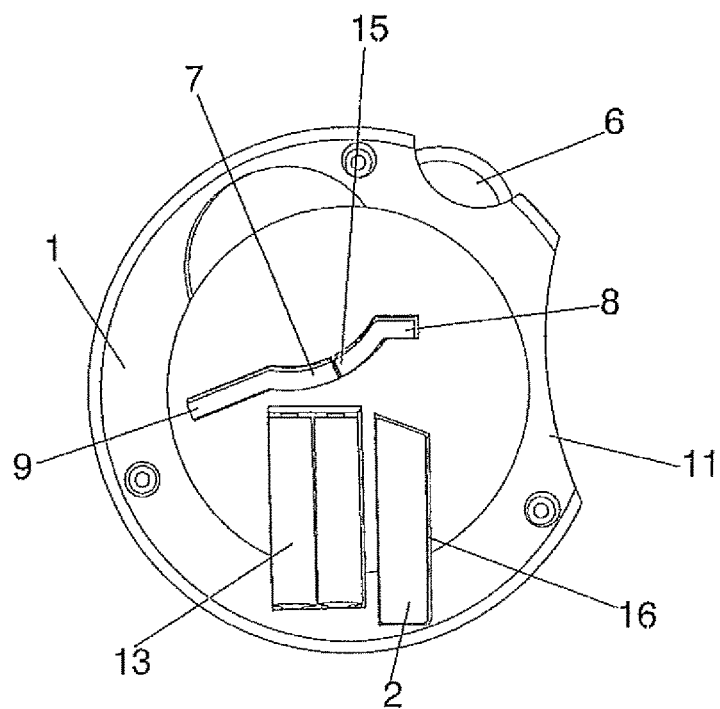

FIG. 2 shows a practical embodiment of the invention, consisting of a portable device for diffusing active ingredients coming from a liquid solution. The device is made up of a casing (1) formed in this case by an upper half and a lower half, which casing is provided with at feast one opening (11) for the passage of air, and a reservoir (2) containing said liquid solution comprising a solvent and at least one type of active ingredient. The device comprises at least one liquid retaining support (not shown) which can be manufactured from a material such as: paper, cardboard, cloth, unwoven cloth, ceramic, carbon fiber, or thermoplastic, and can adopt any shape considered to be suitable for fulfilling its functionality. FIG. 1a shows a support structure (12) on which the retaining support in the form of fabric or paper, for example, is assembled.

The liquid retaining support can be made of a porous material having a liquid absorption capacity of less than 1 g/cm$^3$, and preferably 0.1 g/cm$^3$, Alternatively, the retaining support can be made of a non-porous material, such as a thermoplastic material for example, with the possibility of being structured, i.e. having a rough surface or a surface provided with any type of raised design such as for example lines or grooves preventing the liquid from falling to the floor when it is metered. The device further has dispensing means, consisting in this embodiment of a conventional spray (14) assembled on the reservoir (2), similar to known cologne sprays. These dispensing means (14) are arranged in the casing (1) in a suitable position to dispense doses of the liquid solution on said support, in this case when the spray is pressed. Alternatively, the dispensing means are dripping means which can dispense droplets of the liquid solution, or the dispensing means can meter a dose of liquid solution by means of breaking capsules or microcapsules containing said liquid solution.

The casing (1) has an opening (16) from which the reservoir (2) can be seen from outside, which reservoir can be transparent or translucent such that the user can check the amount of liquid solution remaining in the reservoir, so that the user can perceive when the liquid has run out and substitute the reservoir with a new one.

The liquid retaining support housed inside the casing is arranged between the air outlet (11) and the dispensing means (15).

The device further comprises a fan (17) arranged in said casing in a suitable position to provide an air stream on said liquid retaining support, for the purpose of accelerating the evaporation of the solvent and/or the active ingredient and propel it towards the outside through the outlet (11), The fan is formed by a small direct current motor (4) and an air propelling element (3), in this case in the form a squirrel cage, assembled on the motor shaft.

In another preferred embodiment, the device has conventional heating means (not shown) arranged inside the casing in a suitable position to heat the components of the liquid solution retained by the support at a low temperature. The device includes a push-button (6) assembled in a pivoting manner on a cylindrical shaft (18) fixed to the casing (1) such that a part of this push-button (6) can be accessed from the outside to allow its impulse activation by the user. At its inner part, the push-button (6) has an arm (19) sized and located to press against the spray (14) as can be seen in FIG. 1a, such that the spray expels a dose on the support when the user presses the push-button (6) towards the inside of the casing (1).

The device is provided with an electronic circuit (5) including an electronic timer of a type known by a person skilled in the art. The timer is programmed to a time greater than the time necessary for the evaporation of the solvent and the subsequent evaporation of the active ingredient, which are known beforehand.

In addition, there is a swivel arm or rocker (7), consisting of an arm assembled with the capacity to swivel on a shaft (15) integral with the casing. The rocker (7) has a first end (8) suitably located close to the free end of the arm (19), such that when the push-button (6) is pressed towards the inside of the casing, said arm (19) moves this first end (8) of the rocker downwards, which rocker swivels such that the second end (9) thereof moves upwards. The second end (9) is positioned close to a push-button or switch (not shown) of the electronic circuit (5), such that when said second end (9) moves upwards, it presses said pushbutton, which starts the count of the timer. The free end of the arm (19) is shaped to make contact with the first end (8) of the rocker (7), preferably having a wedge shape which causes, when the pushbutton (6) is pressed, its end fitted inside the casing (1) to reach the contact surface of the first end (8) of the rocker (7), translating the movement of the pushbutton (6) into a shift in reverse directions of each end (8, 9) of said rocker (7). Alternatively, the actuation of said push-button also starts the operation of the fan (17) and/or the heating means, as well as a luminous indicator element, such as an LED for example acting as an element indicating to the user when the previous elements are on or off. The LED remains on during the memorized time for the timer, such that when this time ends, the LED also turns off to indicate to the user that the effect of a dose has ended due to the evaporation of most of the active ingredient, and therefore the user can now start the process again whenever he or she desires by pressing the push-button, activating all the electric components simultaneously as explained below: i) He or she presses the spray to release a single dose of liquid which immediately impregnates the retaining element, ii) He or she activates the electric circuit starting the operation of the fan to project air towards the retaining element in order to favor the evaporation of the liquid absorbed by said retaining element and release the active ingredients into the air through an outlet provided in the casing. iii) At the same instant, the count of the timer of the electric circuit is restarted, this timer being programmed in the factory taking into account the time it takes for the liquid to evaporate completely and for all the concentration of active ingredients comprised in the defined dose to be diffused. iv) If signaling means are provided, at the same time that the timer and the fan start working or when both finish, said signaling means are activated (for example, a luminous indicator turns on or an alarm ringing when the operating time of the timer and the fan turns off), notifying the user that if he or she wants the device to continue operating, he or she can restart the entire process again: spraying-evaporating-timing. Optionally, the process can be automatically started by including actuation means for actuating the push-button in the device itself or by remote control.

In a preferred embodiment, the device has means blocking the operation of the spray, said means being controlled by the timer, such that when a dose of liquid is dispensed on the support, the count of the timer starts and said blocking means are actuated, preventing the spray from being activated again while the timer is still counting. Since the timer is programmed to a time period that is similar to or greater than the time necessary for evaporating most of the solvent and active ingredient from the support, the user is prevented from dispensing a new dose while there is still active ingredient in the support in a sufficient amount to be effective, because the spray is blocked during this time period.

Alternatively, the activation of the spray can be automatic, for which purpose the device has spray actuation means (not shown) causing said activation, which means are also controlled by the timer, such that when the timer finishes its time count, the spray is automatically activated after a pre-established time interval, which can be adjusted by the user, for example, In relation said actuation means, for example, the motor (4) itself could be used to move the pushbutton (6) in a suitable manner to press the spray (14).

The device is portable and powered by battery (13).

In a practical embodiment, the user can choose between a manual or automatic operation, and within the automatic operation, he or she can select various previously programmed metering time intervals according to his or her tastes or needs.

In another alternative embodiment of the invention, the device is not controlled by the timer and does not reproduce the three evaporation phases, i.e. it simply meters active ingredient, but incorporates all the previously described elements; casing, support, dispenser, push-button, fan and heater.

The device can optionally have securing means to be fixed to the body of a person or animal, such as for example a strap, a clip, etc.

Several possibilities of practical embodiments of the invention are described in the attached dependent claims.

In view of this description and set of drawings, a person skilled in the art can understand that the embodiments of the invention which have been described can be combined in many ways within the object of the invention. The invention has been described according to several preferred embodiments thereof but it will be evident for a person skilled in the art that many variations can be introduced in said preferred embodiments without exceeding the object of the claimed invention.

The invention claimed is:

1. A method to evaporate active ingredients from a liquid solution, in which said liquid solution comprises a solvent and at least one type of active ingredient, the method comprising:

dispensing in controlled time periods doses of said liquid solution on a liquid retaining support, wherein the solvent is evaporated from said support such that only the active ingredient remains on the support, and wherein the active ingredient is evaporated from the support after most of the solvent has evaporated;

wherein the time periods between doses are controlled such that a dose of the liquid solution is dispensed on said support at an instant in time after the evaporation of most of the active ingredient of a previous dose from the support;

wherein the solvent and the active ingredient are evaporated at room temperature; and wherein the active ingredient is an insecticide and/or a perfume.

2. A method according to claim 1, wherein the time period between two consecutive doses is greater than the time necessary to evaporate the solvent and the active ingredient from the support.

3. A method according to claim 2, wherein the time period between two consecutive doses is substantially similar to the time necessary to evaporate the solvent and the active ingredient from the support.

4. A method according to claim 1, wherein the time periods between doses are controlled by means of an electronic timer which is associated to electromechanical means to allow dispensing a dose of liquid solution after the established time period between doses.

5. A method according to claim 1, wherein a dose of liquid solution is dispensed by impulse activation by the user.

6. A method according to claim 1, wherein a dose of liquid solution is dispensed automatically in a pre-established time interval.

7. A method according to claim 1, wherein an air stream is applied to the solvent and/or to the active ingredient retained in the support.

8. A method according to claim 1, wherein the doses of liquid solution are dispensed from a liquid reservoir.

9. A method according to claim 1, wherein the doses of liquid solution are dispensed in a coordinated manner in two different liquid retaining supports at different instants in time, such that the active ingredient without solvent is always available in at least one of said supports.

10. A method according to claim 1, wherein the doses of liquid solution are dispensed by means of dripping.

11. A method according to claim 1, wherein the doses of liquid solution are dispensed by means of a spray or an aerosol.

12. A method according to claim 1, wherein the doses of liquid solution are dispensed by means of breaking capsules containing the liquid solution.

* * * * *